(12) United States Patent
Jacobs

(10) Patent No.: US 12,295,999 B2
(45) Date of Patent: May 13, 2025

(54) VACCINE FOR PROTECTION AGAINST STREPTOCOCCUS SUIS

(71) Applicant: Intervet Inc., Rahway, NJ (US)

(72) Inventor: Antonius Arnoldus Christiaan Jacobs, Kessel (NL)

(73) Assignee: Intervet Inc., Rahway, NJ (US)

( * ) Notice: Subject to any disclaimer, the term of this patent is extended or adjusted under 35 U.S.C. 154(b) by 0 days.

(21) Appl. No.: 18/453,684

(22) Filed: Aug. 22, 2023

(65) Prior Publication Data

US 2023/0390376 A1    Dec. 7, 2023

Related U.S. Application Data

(63) Continuation of application No. 16/766,977, filed on May 26, 2020, now abandoned, which is a continuation of application No. PCT/EP2018/084884, filed on Dec. 14, 2018.

(51) Int. Cl.
*A61K 39/09* (2006.01)
*A61K 39/00* (2006.01)
*C12N 9/52* (2006.01)

(52) U.S. Cl.
CPC ...... *A61K 39/092* (2013.01); *A61K 2039/545* (2013.01); *A61K 2039/552* (2013.01); *C12N 9/52* (2013.01)

(58) Field of Classification Search
CPC .................................................. A61K 39/092
See application file for complete search history.

(56) References Cited

U.S. PATENT DOCUMENTS

| | | | | |
|---|---|---|---|---|
| 10,751,403 B2 * | 8/2020 | Jacobs | .................. | A61K 39/092 |
| 11,103,569 B2 * | 8/2021 | Jacobs | .................... | A61P 31/04 |
| 11,167,021 B2 * | 11/2021 | Jacobs | .................. | A61K 39/092 |

FOREIGN PATENT DOCUMENTS

| | | | |
|---|---|---|---|
| JP | | 2017518367 A | 7/2017 |
| WO | WO | 2015181356 A1 | 12/2015 |
| WO | WO | 2017005913 A1 | 1/2017 |
| WO | WO | 2017134274 A1 | 8/2017 |
| WO | WO | 2019115741 A1 | 6/2019 |

OTHER PUBLICATIONS

European Patent Office, European Search Report dated Apr. 11, 2018 for European Patent Application No. 17207758.8 (6 pages).
Iveson et al., 2016, "Health and welfare of pigs before and after weaning," Vet Times, Jul. 18, 2016 (7 pages).
Seele et al., 2015, "The immunoglobulin M-degrading enzyme of Streptococcus suis, IdeSsuis, is a highly protective antigen against serotype 2," Vaccine, 33(19):2207-2212.
Segura, 2015, "Streptococcus suis vaccines: candidate antigens and progress," Expert Rev. Vaccines, 14(12):1587-1608.
Notice of Opposition filed by Intervet International B.V. on Jul. 27, 2021 against European Patent No. EP3148576B1 (10 pages).
Declaration of Antonius Arnoldus Christiaan Jacobs dated Jun. 17, 2021 filed in Opposition against European Patent No. EP3148576B1 by Intervet International B.V. on Jul. 27, 2021 as D3 (4 pages).
Reply to the summons to attend oral proceedings dated Apr. 13, 2022 filed by Intervet International B.V. on Aug. 4, 2022 in Opposition against European Patent No. EP3148576B1 (12 pages).
Grommen et al., 2022, Efficacy of an experimental Streptococcus suis subunit vaccine in pigs against challenge with serotype 9 strain SZ2000-6264, MSD-AH-Boxmeer R&D Laboratories, filed in Opposition against European Patent No. EP3148576B1 by Intervet International B.V. on Aug. 4, 2022 as D15 (4 pages).
European Patent Office, Communication pursuant to Rule 114(2) EPC dated Nov. 10, 2022 regarding transmittal of third party observations filed by Plasseraud IP on Nov. 4, 2022 in European Patent Application No. 18829275.9 (6 pages).
Baums et al., 2010, "Immunogenicity of an autogenous Streptococcus suis bacterin in preparturient sows and their piglets in relation to protection after weaning," Clin. Vaccine Immunol., 17(10):1589-1597.
Hsueh et al., 2017, "Immunization with Streptococcus suis bacterin plus recombinant Sao protein in sows conveys passive immunity to their piglets," BMC Vet. Res., 13(1):15 (9 pages).
Lapointe et al., 2002, "Antibody response to an autogenous vaccine and serologic profile for Streptococcus suis capsular type 1/2," Can. J. Vet. Res., 66(1):8-14.
Seele et al., 2013, "Identification of a novel host-specific IgM protease in Streptococcus suis," J. Bacteriol., 195(5):930-940 (Epub 2012).
Wisselink et al., 2002, "Assessment of protective efficacy of live and killed vaccines based on a non-encapsulated mutant of Streptococcus suis serotype 2," Vet. Microbiol., 84(1-2):155-168.

* cited by examiner

*Primary Examiner* — Brian Gangle
*Assistant Examiner* — Lakia J Jackson-Tongue
(74) *Attorney, Agent, or Firm* — Susanna C. Benn

(57) ABSTRACT

The present invention pertains to a vaccine comprising an immunologically effective amount of an IgM protease antigen of Streptococcus suis, for use in a method for protecting pigs against a pathogenic infection with Streptococcus suis by administering the vaccine only once, wherein the vaccine comprises at most 120 μg per dose of the antigen.

6 Claims, No Drawings

VACCINE FOR PROTECTION AGAINST STREPTOCOCCUS SUIS

CROSS-REFERENCE TO RELATED APPLICATIONS

This application is a continuation Ser. No. 16/766,977, filed on May 26, 2020, which is a national stage entry under 35 U.S.C. § 371 of PCT/EP2018/084884, filed on Dec. 14, 2018, which claims priority to EP17207758.8, filed on Dec. 15, 2017, the content of PCT/EP2018/084884 is hereby incorporated by reference in its entirety.

GENERAL FIELD OF THE INVENTION

The invention pertains to the protection of pigs against a pathogenic infection with *Streptococcus suis*.

BACKGROUND OF THE INVENTION

*Streptococcus suis* is a commensal and opportunistic pathogen of swine. In particular under stress, the bacterium may elicit a pathogenic infection and induce disease. Under modern pig producing conditions, major stress is induced for example by weaning of piglets and transport of young piglets. This has made *Streptococcus suis* to become a major swine pathogen. It is also an emerging zoonotic agent of human meningitis and streptococcal toxic shock-like syndrome. *Streptococcus suis* is a well-encapsulated pathogen and multiple serotypes have been described based on the capsular polysaccharide antigenic diversity. *Streptococcus suis* uses an arsenal of virulence factors to evade the host immune system. Together, these characteristics have challenged the development of efficacious vaccines to fight this important pathogen. Recently, an overview article has been published regarding vaccines against *Streptococcus suis* (Mariela Segura: "*Streptococcus suis* vaccines: candidate antigens and progress, in Expert Review of Vaccines, Volume 14, 2015, Issue 12, pages 1587-1608). In this review, clinical field information and experimental data have been compiled and compared to give an overview of the current status of vaccine development against *Streptococcus suis* as outlined here below.

Currently used vaccines are mainly whole-cell bacterins. However, field reports describe difficulty in disease control and management, and specially "vaccine failures" are common. Carrier pigs are the primary source of infection, and both vertical and horizontal transmission are involved in spread of the disease within a herd. Mixing of carrier animals with susceptible animals under stressful conditions such as weaning and transportation usually results in clinical disease. Early medicated weaning and segregated early weaning practices do not eliminate *Streptococcus suis* infection. Therefore, effective control measures to prevent disease will hinge on prophylactic/metaphylactic procedures (where allowed) and on vaccination. Currently, field immunization efforts have focused on the use of commercial or autogenous bacterins. These vaccine strategies have been applied to either piglets or sows. From weaning and onwards piglets are more susceptible to *Streptococcus suis* infections due to the stresses associated with weaning and also, the common subsequent transport. Therefore, prepartum immunization in sows is often used to try and convey passive immunity to piglets and provide protection against *Streptococcus suis* under these stressful circumstances early in life. Moreover, sow vaccination is less costly and labor intensive, thus representing an economical alternative to piglet vaccination. Yet, available results seem to indicate that sow vaccination with bacterins is also a matter of controversy. In many cases vaccinated sows, even when vaccinated twice before parturition, respond poorly or not at all to vaccination which results in low maternal immunity transferred to the litters. And even if maternal immunity is transferred at a sufficient level, in many cases the maternal antibodies are too low to provide protection in the most critical period of 4-7 weeks of age.

In pigs, autogenous bacterins are frequently used in the field, especially in Europe. They are prepared from the virulent strain isolated on the farm with clinical problems and applied to the same farm. One of the disadvantages of autogenous bacterins is that vaccine safety data are lacking and severe adverse reactions may occur. Sampling errors (due to using only one or two pigs or samples) may result in failure to identify a strain or serotype associated with a recent outbreak. This failure may be especially problematic in endemic herds. Finally, the most important dilemma of autogenous bacterins is that their actual efficacy has been poorly studied. As application of autogenous vaccines is empirical, it is not surprising that results obtained with these vaccines are inconsistent.

Other experimental vaccines are also described in the art. Kai-Jen Hsueh et al. show ("Immunization with *Streptococcus suis* bacterin plus recombinant Sao protein in sows conveys passive immunity to their piglets", in: *BMC Veterinary Research*, BMC series—open, inclusive and trusted, 13:15, 7 Jan. 2017) that a bacterin plus subunit might be a basis for successful vaccination of sows to confer protective immunity to their piglets.

Live attenuated vaccines have also been contemplated in the art. Non encapsulated isogenic mutants of *Streptococcus suis* serotype 2 have been clearly shown to be avirulent. Yet, a live vaccine formulation based on a non encapsulated serotype 2 mutant induced only partial protection against mortality and failed to prevent the development of clinical signs in pigs challenged with the wildtype strain (Wisselink H J, Stockhofe-Zurwieden N, Hilgers L A, et al. "Assessment of protective efficacy of live and killed vaccines based on a non-encapsulated mutant of *Streptococcus suis* serotype 2." in: *Vet Microbiol*. 2002, 84:155-168.)

In the last couple of years, an extensive list of antigenic or immunogenic *Streptococcus suis* molecules has been reported, and most of these have been discovered through immuno proteomics using either convalescent sera from infected pigs or humans and/or laboratory-produced immune sera. WO2015/181356 (IDT Biologika GmbH) has shown that IgM protease antigens (either the whole protein or the highly conserved Mac-1 domain representing only about 35% of the full protein) can elicit a protective immune response in piglets in a vaccination scheme of administering two doses of the IgM protease antigen, optionally in combination with a prime vaccination containing a bacterin. It is noted that WO2017/005913 (Intervacc AB) also describes the use of an IgM protease antigen (in particular, an IgM protease polypeptide fused to a nucleotidase) but only the property of being able to elicit a seroresponse has been shown. A protective effect for an IgM protease antigen is not shown in this international patent application.

Object of the Invention

It is an object of the invention to find an improved vaccination strategy to protect a pig against a pathogenic infection with *Streptococcus suis*.

SUMMARY OF THE INVENTION

In order to meet the object of the invention a vaccine comprising an immunologically effective amount of an IgM protease antigen of *Streptococcus suis* has been devised for use in a method for protecting pigs by administering the vaccine only once, wherein the vaccine comprises at most 120 µg per dose of the antigen.

The antigen of this vaccine is known i.a. from WO2015/181356 and WO2017/005913. However, as indicated here above, it is not clear from any of these references whether the IgM protease antigen as such is able to elicit a protective immune response in a one shot approach. In WO2015/181356 a two-shot vaccination approach is used in combination with a bacterin, wherein about 250 µg of the IgM protease is used. Therefore, it came as a surprise that the IgM protease antigen on itself, at less than half of the dose as known from WO2015/181356, and by administering only one shot of the antigen, is able to elicit a protective immune response that protects the pigs against a pathogenic infection with *Streptococcus suis*. In this respect it is important to acknowledge that in the art, non-live *Streptococcus suis* vaccines have always been administered in a prime-boost regime. Also, in the art (see WO2015/181356 and WO2017/005913) the antigen for use in the current invention, has consistently proposed to use this antigen in a two-shot administration approach, optionally even using a multi-way vaccine (i.e. more than only the IgM protease antigen alone). It was therefore highly surprising to see that a single dose of the IgM protease antigen as such, using less than half of the amount used in the art, is able to induce protective immunity.

The new vaccination strategy has multiple advantages. Apart from the fact that using significantly less antigen is advantageous from an economical point of view, the safety of a vaccine comprising less antigen is generally improved. Too much antigen can lead to unwanted immunological effects such as an anaphylactic shock. Also, by needing to administer the antigen only once, the animals get less stressed by the vaccination process.

For the present invention, it was established that using 120 µg per dose in the vaccine, an effective protective immune response could still be obtained. Per definition, 120 µg per dose thus is an immunologically effective amount of the antigen. The lower limit of the immunologically effective amount can be established by performing a common dose response study and assessing at what dose a desired protection (e.g. a decreased mortality of piglets) can still be arrived at. The lower limit is thus also determined by the desired level of protection. Based on the finding that at a dose as low as 4.4 µg still the same level of protection can be obtained when compared to using 120-250 µg, and thus, no decrease in protective response is yet seen, it is expected that at a dose of 1 or even only 0.1 µg of the antigen, still a practical relevant protective effect can be observed. Thus, for the current vaccine, a practical minimum immunological effective amount is believed to be 0.1 µg of the antigen per dose, but any higher dose such as 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or any higher integer in the range 61-119 up to 120 µg per doses may be used in line with the present invention.

The invention also pertains to the use of an IgM protease antigen of *Streptococcus suis* for the manufacture of a vaccine for protecting pigs against a pathogenic infection with *Streptococcus suis* by administering the vaccine only once, wherein the vaccine comprises an immunologically effective amount of the IgM protease antigen of at most 120 µg per dose, and to a method for protecting pigs against a pathogenic infection with *Streptococcus suis* by administering a vaccine comprising an immunologically effective amount of an IgM protease antigen of *Streptococcus suis* only once, wherein the vaccine comprises at most 120 µg of the antigen per dose.

It is noted that in the vaccine according to the invention the antigen is typically combined with a pharmaceutically acceptable carrier, i.e. a biocompatible medium, viz. a medium that after administration does not induce significant adverse reactions in the subject animal, capable of presenting the antigen to the immune system of the host animal after administration of the vaccine. Such a pharmaceutically acceptable carrier may for example be a liquid containing water and/or any other biocompatible solvent or a solid carrier such as commonly used to obtain freeze-dried vaccines (based on sugars and/or proteins), optionally comprising immunostimulating agents (adjuvants). Optionally other substances such as stabilisers, viscosity modifiers or other components are added depending on the intended use or required properties of the vaccine.

Definitions

A vaccine is a pharmaceutical composition that is safe to administer to a subject animal, and is able to induce protective immunity in that animal against a pathogenic micro-organism, i.e. to induce a successful protection against the micro-organism.

An IgM protease antigen of *Streptococcus suis* is an enzyme that specifically degrades porcine IgM (and not porcine IgG or porcine IgA; Seele at al, in *Journal of Bacteriology*, 2013, 195 930-940; and in *Vaccine* 33:2207-2212; 5 May 2015), a protein denoted as IdeS suis, or an immunogenic part thereof (typically having a length of at least about 30-35% of the full length enzyme). The whole enzyme has a weight of about 100-125 kDa, corresponding to about 1000-1150 amino acids, the size depending on the serotype of *S. suis*. In WO 2015/181356 several sequences that represent an IgM protease antigen of *Streptococcus suis* are given, viz. SEQ ID NO:1, SEQ ID NO:2, SEQ ID NO:6, SEQ ID NO:7 and SEQ ID NO:5, the latter being an immunogenic part of the full length enzyme (denoted as the Mac-1 domain, i.e. amino acids 80-414 of SED ID NO:7). Other examples of immunogenic parts of the full length enzyme are given in WO2017/005913. In particular the IgM protease may be the protease according to SEQ ID NO:1 of WO2015/1818356 or a protein having at least 90%, or even 91, 92, 93, 94, 95, 96, 97, 98, 99% up to 100% sequence identity in the overlapping regions. The amino acid sequence identity may be established with the BLAST program using the blastp algorithm with default parameters. It is expected that the IgM protease of *Streptococcus suis* of various serotypes have a sequence identity higher than 90%, in particular expected to be 91, 92, 93, 94, 95, 96, 97, 98, 99% up to 100%. An artificial protein, for example made to optimize yield in a recombinant production system of the antigen, may lead to a lower amino acid sequence identity such as 85%, 80%, 75%, 70% or even 60% compared with the whole enzyme, while maintaining the required immunogenic function, and is understood to be an IgM protease antigen of *Streptococcus suis* in the sense of the present invention.

Protection against a pathogenic infection with a micro-organism is aiding in preventing, ameliorating or curing the pathogenic infection with that micro-organism or a disorder arising from that infection, for example to prevent or reduce one or more clinical signs resulting from the infection with the pathogen.

A vaccination method wherein the vaccine is administered only once means that protective immunity is conferred after only one single shot of the vaccine, and thus, that a booster vaccination is omitted to arrive at the said protective immunity. In a two-shot regime, the first (prime) vaccination is typically boosted within 6 weeks from the first administration, commonly within 3 or even 2 weeks from the first administration, and only after the second (boost) administration protective immunity, i.e. a successful protection as defined here above, is understood to be obtained.

An immunological effective amount of an antigen is an amount that is capable of eliciting protective immunity in a subject animal.

EMBODIMENTS OF THE INVENTION

In an embodiment of the vaccine for use according to the invention, the method comprises administering the vaccine to the pigs at an age of at most 28 days. In the art there is the general concern that pigs, in particular when younger than 28 days when vaccinated, do not have a mature adaptive immune system and thus, that arriving at protective immunity might be impaired. However, it was found that when using the IgM protease antigen in line with the new vaccination strategy (low dose, one shot), is able to elicit adequate protective immunity. The age of vaccination with the IgM protease antigen can be any age of 1, 2, 3, 4, 5, 6, 7, 8, 9, 10, 11, 12, 13, 14, 15, 16, 17, 18, 19, 20, 21, 22, 23, 24, 25, 26, 27 or 28 days. As is known form the art, in particular from WO2017/005913, a positive immune response against an IgM protease antigen can be obtained in young pigs from the day of birth and onwards. This means that by the present showing of actual protection in 3 week old pigs, it is understood that protection can be obtained even at a younger age.

In another embodiment the method comprises administering the vaccine before an age at which the pigs are weaned. In other words, the vaccine is administered before the piglets are actually weaned. It has been shown that the vaccination at this early age, can protect against a pathogenic infection with *Streptococcus suis*, induced by stress within a short window of 2-3 weeks right after weaning. This was not beforehand expected since a potential protective effect of the IgM protease antigen as such is only known (see WO2015/181356) for animals that have passed the critical stage of 2-3 weeks after weaning, namely at an age of 5-7 weeks at vaccination, well after the period in which the animals were stressed due to weaning. It is known that the critical period for getting a pathogenic infection with *Streptococcus suis* is right after weaning. So any successful vaccination strategy in healthy animals after the weaning process was completed and stress was no longer involved, does not provide any proof of successful vaccination against *Streptococcus suis* before the animals are weaned.

In yet another embodiment the method comprises administering the vaccine to pigs having maternally derived anti-*Streptococcus suis* antibodies. Active vaccination of very young pigs has the concern of possible interference with maternal antibodies, either produced by natural infection or by active immunization of sows (Baums C G, Bruggemann C, Kock C, et al. "Immunogenicity of an autogenous *Streptococcus suis* bacterin in preparturient sows and their piglets in relation to protection after weaning", in: *Clin Vaccine Immunol*. 2010; 17:1589-1597). Indeed, neither vaccination of suckling nor of weaning piglets from immunized sows was associated with a prominent active immune response and protection at 8 weeks of age. This failure was associated with a strong inhibitory effect of maternal antibodies or other colostrum components. In this regard, interference between maternal antibodies and active production of antibodies against *S. suis* could also be demonstrated in a field study after vaccination with an autogenous *S. suis* capsular type 1/2 vaccine formulation (Lapointe L, D' Allaire S, Lebrun A, et al.: "Antibody response to an autogenous vaccine and serologic profile for *Streptococcus suis* capsular type 1/2." in: *Can J Vet Res*. 2002; 66:8-14. A field study aimed at determining the efficacy of a single-dose *S. suis* serotype 14 bacterin protocol in 4-day-old suckling piglets also failed to protect piglets against homologous challenge (Amass S F, Stevenson G W, Knox K E, et al. "Efficacy of an autogenous vaccine for preventing streptococcosis in piglets" in: *Vet Med*. 1999, 94, 480-484. Surprisingly, it has been found that by using the IgM protease antigen at a low dose and administering only one shot of the antigen, interference with maternal anti-Ssuis antibodies is not a problem for arriving at protection against a pathogenic infection with *Streptococcus suis*. This provides the unique option to vaccinate the piglets themselves and induce active protection, instead of relying on the short live passive protection that can be obtained via the colostrum of immunised mother animals. It has been shown that the vaccination may even take place before the piglets are weaned in order to have them protected against a disease resulting from *Streptococcus suis*, induced by the stress of weaning or the transportation of young animals right or soon after the weaning procedure. For the first time now, an antigen that was shown to have a potential protective effect in older animals, in which animals interference with MDA's is typically not a problem, has been shown to be useful for vaccinating MDA positive animals to arrive at a clear protective effect induced by stress at an early age, typically in the window of 2-3 weeks after weaning. It is noted that the data in WO2015/181356 only show successful vaccination in piglets having an age of 5-7 weeks and receiving a challenge infection at an age of 9 weeks, thus well after the risk period (i.e. the period of peak incidence of pathogenic *Streptococcus suis* infections) of 2-3 weeks after weaning, i.e. 5-7 weeks of age. There is no indication whether the IgM protease antigen is able to overcome the common problem of interference with maternal immunity. On the contrary, the choice of animals being vaccinated at an age of 5-7 weeks, is a clear indication that the interference with MBA's, if present, was meant to be avoided.

In still another embodiment the vaccine is for conferring protection against mortality associated with a pathogenic infection with *Streptococcus suis*.

In yet another embodiment the vaccine is for conferring protection against clinical signs associated with a pathogenic infection with *Streptococcus suis*. Typical clinical signs associated with a pathogenic infection with *Streptococcus suis* are increased rectal temperature, impaired locomotion (limping, swollen joints), increased respiration rate and neurological signs (e.g. tremors, convulsions, torticollosis, ataxia). Preventing, amelioration or curing one or more of these signs will be beneficial for the pig, not only since it is an indication that the pathogenic infection is being suppressed.

The invention will now be further explained based on the following non-limiting examples.

EXAMPLES

Example 1

The objective of this experiment was to test the dose-response efficacy of a one-shot low dose (120 μg or less per dose; as determined by a Bradford protein assay using bovine serum albumin as a standard) IgM protease vaccine against *Streptococcus suis* challenge.

Study Design

For this study, fifty 3-week-old piglets were used. The piglets were allotted to five groups (different litters evenly distributed over the groups) of 10 piglets each. Group 1 to 4 were vaccinated once intramuscularly at 3 weeks of age with either of the different vaccine doses, i.e. 120 μg, 40 μg, 13.3 μg and 4.4 μg respectively of the recombinant rIdeSsuis IgM protease antigen (see par 2.2. of Seele et al. in *Vaccine* 33:2207-2212 for the used antigen) per dose, formulated in a water-in-oil adjuvant. Group 5 was left as unvaccinated challenge control. At 4 weeks of age the piglets were weaned. At 6 weeks of age the piglets were transported to the challenge room and challenged immediately. There was no acclimatization period between the transport and the challenge to mimic natural stress. After challenge the pigs were observed daily for clinical signs of *S. suis* infection (such as depression, locomotory problems and/or neurological signs) and scored using a regular scoring system going from 0 (no signs) to 3 for severe cases. Severely affected animals were euthanized and post-mortem examined. At the end of the study (7 days after challenge) all surviving pigs were euthanized and post-mortem examined. Just before vaccination and challenge, serum blood was collected for antibody determination. At regular times before and after challenge heparin blood was collected for re-isolation of the challenge strain.

Results

None of the vaccines induced any unacceptable site or systemic reactions and thus could be considered safe. On day of vaccination (3 weeks of age) most pigs were sero-negative or had a low maternally derived antibody titre. After vaccination, all vaccine groups showed antibody responses and a clear serological dose-response effect was observed with average group titers of 6.5, 6.0, 4.9, 4.4 and 3.5 $\log_2$, respectively. The results for the different parameters post-challenge are shown below in Table 1.

TABLE 1

Post challenge data study 1

| Group | Avg survival time (days) | Avg clinical score | Avg blood reisol score | # pos. blood | Dead after challenge |
|---|---|---|---|---|---|
| 1 | 6.7 | 9.2 | 0.7 | 3/10 | 2/10 |
| 2 | 6.5 | 8.6 | 0.2 | 1/10 | 1/10 |
| 3 | 6.6 | 7.7 | 0.8 | 2/10 | 1/10 |
| 4 | 6.6 | 7.4 | 0.3 | 1/10 | 1/10 |
| 5 | 5.1 | 30.9 | 1.7 | 6/10 | 6/10 |

Conclusion

The results demonstrate that all four vaccine doses of the one-shot IgM protease vaccine induced protection in 3-week-old piglets, partly (about 20% on average) MDA positive) against a challenge with pathogenic *Streptococcus suis* 3 weeks after vaccination. The level of protection appeared to correspond to the level of protection obtainable when using a two shot approach with 250 μg of the IgM protease per shot (500 μg in total per animal; as used in WO2015/181356). No dose-response effect was observed and a vaccine dose as low as 4.4 μg showed convincing protection at least at the same level (or even better) than when using 120 μg of the antigen. Based on this it is believed that a lowest practical dose could be as low as 1.0 μg or even 0.1 μg of the IgM protease.

Example 2

As protection against *Streptococcus suis* for pigs is preferably obtained even when the animals have maternally derived antibodies directed against *Streptococcus suis*, it was assessed whether an IgM protease containing vaccine is efficacious as a one shot vaccine in maternally derived anti-*Streptococcus suis* positive pigs at an age of 3 weeks.

Study Design

For this study 2 groups of 10 pigs each were used. Group 1 consisted of 3 week old anti-Ssuis MDA positive piglets (only 1 out of 10 animals appeared to have an MDA level below detection limit). These animals were vaccinated once intramuscularly with the IgM protease antigen formulated in an oil-in-water adjuvant. Group 2 served as a negative challenge control group. At 4 weeks of age the piglets were weaned. At 6 weeks of age the piglets were transported to the challenge room and challenged immediately. The piglets were challenged with a virulent culture of *Streptococcus suis* serotype 2. At regular times before and after challenge heparin blood was collected for re-isolation of challenge strain. After challenge the pigs were observed daily for clinical signs of *S. suis* infection. Severely affected animals were euthanized and post-mortem examined. At the end of the study (7 days after challenge) all surviving pigs were euthanized and post-mortem examined.

Results

The vaccines did not induce any unacceptable site or systemic reactions. The post challenge data for the period before euthanisation (at day 7) are indicated in Table 2. On the day of challenge one pig in Group 2 appeared to be a runt and it was decided not to challenge this animal. The average clinical scores, the number of dead animals after challenge and the number of animals that allowed re-isolation of the pathogen from the blood were significantly improved due to vaccination.

TABLE 2

Post challenge data Study 2

| Group | Average clinical score | Dead after challenge | Positive blood isolation |
|---|---|---|---|
| 1 | 18 | 3/10 | 3/10 |
| 2 | 43 | 7/9 | 7/9 |

Conclusion

In conclusion, the results demonstrate that by administering the IgM protease antigen only once, adequate protection can be induced in 25-days-old MDA positive piglets against a pathogenic infection with *Streptococcus suis*, even when the animals are challenged 3 weeks after vaccination, 2 weeks after weaning and immediately after transport. Although this has been demonstrated with a dose of 250 μg, since example 1 shows that the antigen is capable of inducing the same level of protection, or stronger, even the best level of protection at an antigen dose as lows as 4.4 μg, it is understood that comparable results are obtained when aiming at protection in MDA positive piglets with doses of 120 μg or below.

The invention claimed is:

1. A method for protecting a pig against a pathogenic infection with *Streptococcus suis* by administering a vaccine comprising an immunologically effective amount of an IgM protease antigen of *Streptococcus suis* only once to the pig, wherein the vaccine comprises at most 120 µg of the antigen per dose.

2. The method of claim 1, wherein the administering of the vaccine to the pig is performed when the pig is at an age of at most 28 days.

3. The method of claim 1, wherein the administering of the vaccine to the pig is performed before the pig is at an age at which the pig is weaned.

4. The method of claim 1, wherein the pig has maternally derived anti-*Streptococcus suis* antibodies.

5. The method of claim 1, wherein the method of administering of the vaccine to the pig is for conferring protection against mortality associated with a pathogenic infection with *Streptococcus suis*.

6. The method of claim 1, wherein the method of administering of the vaccine to the pig is for conferring protection against clinical signs associated with a pathogenic infection with *Streptococcus suis*.

* * * * *